United States Patent
Stahl et al.

(10) Patent No.: US 10,844,009 B2
(45) Date of Patent: Nov. 24, 2020

(54) PROCESS FOR PREPARING GUANIDINO ACETIC ACID

(71) Applicant: Evonik Operations GmbH, Essen (DE)

(72) Inventors: Timo Stahl, Limeshain (DE); Patrik Stenner, Hanau (DE); Cornelia Borgmann, Frankfurt (DE); Christian Renner, Gründau (DE); Axel Ronneburg, Hanau (DE)

(73) Assignee: Evonik Operations GmbH, Essen (DE)

(*) Notice: Subject to any disclaimer, the term of this patent is extended or adjusted under 35 U.S.C. 154(b) by 0 days.

(21) Appl. No.: 16/731,551

(22) Filed: Dec. 31, 2019

(65) Prior Publication Data

US 2020/0207707 A1 Jul. 2, 2020

(30) Foreign Application Priority Data

Jan. 2, 2019 (EP) .................................. 19150078

(51) Int. Cl.
*C07C 277/08* (2006.01)

(52) U.S. Cl.
CPC .................................. *C07C 277/08* (2013.01)

(58) Field of Classification Search
None
See application file for complete search history.

(56) References Cited

U.S. PATENT DOCUMENTS

| 4,126,664 A | 11/1978 | Weiss |
| 8,501,810 B2 | 8/2013 | Gastner |
| 2009/0163739 A1* | 6/2009 | Thalhammer ......... C07C 277/08 562/560 |

FOREIGN PATENT DOCUMENTS

| CN | 1470502 | 1/2004 |
| CN | 101462983 | 6/2009 |
| CN | 102329250 | 1/2012 |

OTHER PUBLICATIONS

Extended European Search Report for EP 19 15 0078, filed Jan. 2, 2019, for corresponding U.S. Appl. No. 16/731,551.
Strathmann, et al., "Die Elektrodialyse—ein Membranverfahren mit vielen Anwendungsmöglichkeiten," *Chmiel. Chem. Ing. Tech.* 56(3):214-220 (1984); with English language abstract on p. 1 of the article itself.

* cited by examiner

*Primary Examiner* — Sudhakar Katakam
*Assistant Examiner* — Jennifer C Sawyer
(74) *Attorney, Agent, or Firm* — Law Office of: Michael A. Sanzo, LLC

(57) ABSTRACT

The present invention pertains to a process for preparing guanidino acetic acid (GAA) from cyanamide and glycine in alkaline process solution, in which anionic impurities are removed from the process solution by electrodialysis.

20 Claims, 2 Drawing Sheets

PROCESS FOR PREPARING GUANIDINO ACETIC ACID

CROSS REFERENCE TO RELATED APPLICATIONS

The present application claims priority under 35 USC § 119 to European application, EP 19150078.4, filed on Jan. 2, 2019, the contents of which is incorporated herein by reference in its entirety.

FIELD OF THE INVENTION

The present invention pertains to a process for preparing guanidino acetic acid (GAA) from cyanamide and glycine in alkaline process solution.

BACKGROUND OF THE INVENTION

Guanidino acetic acid (GAA) is a colorless, nitrogenous organic compound used as an animal feed additive (EP 1 758 463 B1). GAA is the direct natural precursor of creatine. The supplementation of GAA allows an optimal supply of creatine in the organism, which in turn positively influences the energy transport in the muscle cells.

The production of GAA was first described in 1861 by the addition of cyanamide to glycine (M. Strecker, compt. rend. 1861, 52, 1212). A weakly caustic aqueous ammonia solution was used as the reaction medium. Recent publications include reaction conditions with sodium hydroxide (CN 102329250) solution or sodium carbonate (CN 101462983) as base for pH adjustment. GAA synthesis can be performed batchwise or as a semi-continuous or continuous process. Cyanamide is usually reacted with excess glycine in alkaline process solution, the guanidino acetic acid product is separated off via filtration and the alkaline process solution comprising glycine is recirculated.

Although the optimum pH value for the reaction of glycine with cyanamide is in the slightly alkaline range, the reaction of cyanamide with itself to form dicyandiamide (DCA) also occurs under the same reaction conditions. This side reaction can be suppressed by using an excess of glycine. For a recovery of the excess glycine after the reaction is complete, a process design with recirculation of the glycine-containing filtrate after separation of GAA is particularly suitable.

Usually, aqueous cyanamide solutions are mixed with acids such as phosphoric acid or formic acid or formic acid esters for stabilization and pH adjustment (DE 26 42 023). Under the alkaline environment of the GAA process conditions, these acids are converted into water-soluble salts. Accordingly, the aforementioned recirculation leads to the accumulation of salts originating from cyanamide stabilization. Separating off these salts by means of a purge stream would also lead to a significant loss of glycine due to the high glycine concentrations and the high glycine solubility.

Another challenge relates to the purity of the glycine used in the GAA process. At present, glycine of technical quality (TG-glycine) is not suitable for continuous GAA production processes, as the impurities contained therein also accumulate. Due to the glycine manufacturing process, chloride is a common contaminant. Chloride can reach such high concentrations that the reactors are attacked by corrosion or pitting corrosion.

Electrodialysis (EDI) is a process in which ionic constituents of an aqueous solution are removed by means of ion exchange membranes and an electrical potential difference. Electrodialysis is a known method for processing wastewaters or for desalinating water. A further field of use is, for example, the separation of amino acids having different isoelectric points in electrodialysis cells, the chambers or compartments of which are separated from one another by anion and cation exchange membranes, at different pH values under the influence of the electric field (H. Strathmann and H. Chmiel, Chem. Ing. Tech, 56 (1984) No. 3, 214-220).

However, in EDI processes, metal contaminants can damage the expensive membranes and significantly reduce their lifetime. Furthermore, the glycine and other valuable substances in the GAA process are ionic and thus charged, so that it would be assumed that, in addition to the targeted separation of the chloride, valuable substances would also be lost. Therefore, the skilled artisan would find no motivation in the prior art or in common general knowledge to apply an electrodialysis step to the GAA process.

It was the objective of the present invention to provide a process for preparing guanidino acetic acid (GAA), which comprises the steps of reacting cyanamide with excess glycine in alkaline process solution, separating off the guanidino acetic acid product and recirculating the alkaline process solution comprising glycine, in which, by suitable measures, the concentration of anionic impurities—such as chloride and/or phosphate—are lowered, such that the enrichment or accumulation of these anionic impurities in the alkaline process solution can be prevented.

SUMMARY OF THE INVENTION

This objective is achieved by a process for preparing guanidino acetic acid (GAA), the process comprising (a) preparing an alkaline process solution comprising glycine, (b) reacting cyanamide with the excess glycine as comprised in the alkaline process solution, (c) separating off the guanidino acetic acid product and (d) recirculating the alkaline process solution comprising glycine; wherein anionic impurities are removed from the process solution by electrodialysis, wherein the electrodialysis is conducted in a cell comprising at least one feed compartment comprising the alkaline process solution and at least one concentrate compartment, and wherein the pH of the alkaline process solution is between 8.5 and 11.

Anion exchange membranes are abbreviated as "AEM" and cation exchange membranes are abbreviated as "CEM".

Figure 4:
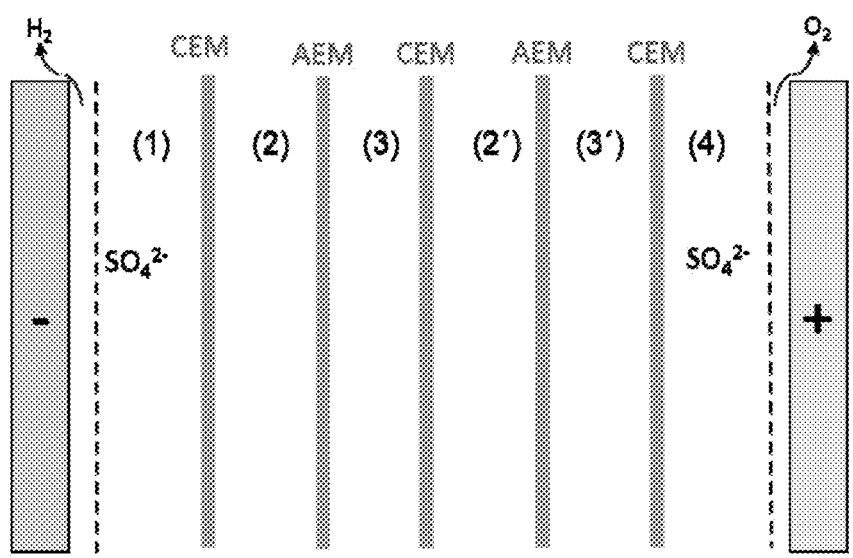

FIG. 4 depicts an electrodialysis cell including outer compartments (1) and (4) comprising a sulfuric acid solution; feed compartments (2), (2'); and concentrate compartments (3), (3'). Anion exchange membranes are abbreviated as "AEM" and cation exchange membranes are abbreviated as "CEM".

DETAILED DESCRIPTION OF THE INVENTION

The inventors have unexpectedly found that the aforementioned drawbacks in the GAA process caused by the enrichment of anionic impurities, such as chloride, in the alkaline process solution can be overcome by including an electrodialysis (EDI) step within the GAA process.

Accordingly, the present invention pertains to a process for preparing guanidino acetic acid (GAA), the process comprising (a) preparing an alkaline process solution comprising glycine, (b) reacting cyanamide with the excess glycine as comprised in the alkaline process solution, (c) separating off the guanidino acetic acid product and (d) recirculating the alkaline process solution comprising glycine; wherein anionic impurities are removed from the process solution by electrodialysis, wherein the electrodialysis is conducted in a cell comprising at least one feed compartment comprising the alkaline process solution and at least one concentrate compartment, and wherein the pH of the alkaline process solution is between 8.5 and 11.

In addition to the above, the process of the present invention also provides the advantage that the risk of corrosion and the unwanted discharge of glycine are significantly reduced.

Further, technical grade glycine may be used within the new GAA process. Besides chloride, also cyanamide stabilizers may be removed from the alkaline process solution via EDI without losing glycine. Accordingly, the invention also leads to a significant reduction in manufacturing costs.

Electrodialysis also separates off other salts and metal ions. This allows the process solutions used to be kept constant over a longer period of time than before, even within the reaction cycle. This further improves process stability.

In process step a), an alkaline solution of glycine is prepared. The pH of said alkaline solution is between 8.5 and 11, preferably between 9 and 10. The pH may be adjusted using inorganic alkaline compounds, such as ammonia, sodium carbonate or sodium hydroxide.

The concentrate compartment comprises an aqueous solution of an inorganic salt ("concentrate solution"), such as alkali or alkaline earth metal chlorides or sulfates. Solutions of sodium chloride or potassium chloride are particularly suitable.

In a preferred embodiment, sodium chloride is used as the concentrate solution.

Figure 3:
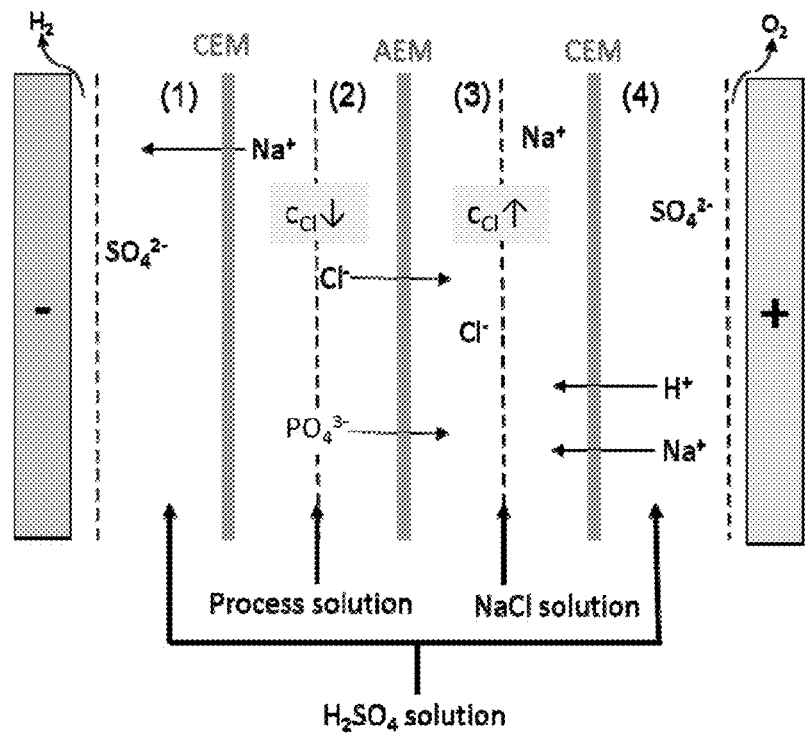
FIG. 3 depicts an electrodialysis cell including outer compartments (1) and (4) comprising a sulfuric acid solution; feed compartment (2); and concentrate compartment (3).

The at least one feed compartment (2) is preferably interconnected with the at least one concentrate compartment (3) by an ion-selective anion exchange membrane (AEM), as depicted in FIGS. 3 and 4.

The at least one feed compartment (2) and the at least one concentrate compartment (3) may be each independently connected with an another compartment by an ion-selective cation exchange membrane (CEM).

The concentrate starting solution (preferably: brine starting solution) should have an initial conductivity of at least 100 µS/cm, in particular at least 1 mS/cm and preferably at least 50 mS/cm.

The maximum concentration of the salt solution (NaCl) should be less than 500 g/l, in particular less than 100 g/l and preferably less than 20 g/l.

The electrodialysis cell may comprise a stack of alternating feed compartments (2, 2') and concentrate compartments (3, 3'), the compartments being formed by alternating an ion-selective anion exchange membranes and ion-selective cation exchange membranes, as depicted in FIG. 4.

Alternatively, the electrodialysis cell may be configured as a four-compartment cell, the compartments being interconnected by three ion-selective exchange membranes. Therein, two ion-selective cation exchange membranes are directed towards the electrodes and the ion-selective anion exchange membrane is located in the center of the electrodialysis cell, as depicted in FIG. 3.

The electrodialysis cell preferably comprises two outer compartments comprising an aqueous solution of sulfuric acid, each compartment being located between an electrode and the outer ion-selective cation exchange membrane.

The aqueous solution of sulfuric acid may have concentrations of between 0.05 mol/l and 1 mol/l. Preferably, the concentration of sulfuric acid is about 0.5 mol/l. The conductivity of the sulfuric acid solution should be at least 50 mS/cm, in particular at least 100 mS/cm and preferably at least 200 mS/cm.

The pH of the alkaline process solution is between 8.5 and 11, and preferably between 9 and 10. In a particularly preferred embodiment, the pH of the alkaline process solution is around 9.5.

The cyanamide is introduced into the process as an aqueous solution. The concentration of cyanamide therein is in general between 10 wt. % and 70 wt. %. Said aqueous solution preferably comprises at least one stabilizing agent.

Said at least one stabilizing agent may be present in an amount of between 0.005 wt. % and 3 wt. %, based on the cyanamide solution.

The at least one stabilizing agent may be selected from inorganic acids, organic acids, esters of organic acids, inorganic salts, preferably from alkaline earth metals, such as magnesium chloride or magnesium sulfate, or combinations thereof. Stabilizing agents selected from the group consisting of phosphoric acid, formic acid, esters of formic acid, magnesium chloride, magnesium sulfate, and mixtures of these compounds are particularly preferred.

For process step (b), the ratio of cyanamide to glycine is in the range of between 1.1:1 and 10:1, preferably in the range of between 1.5:1 and 2.5:1.

In process step b), the GAA product is formed as a solid that can e.g. be separated off by precipitation or filtration (process step c)). Filtration is, due to its simplicity and compatibility to the process, particularly preferred.

The remaining liquid phase (filtrate), i.e. the remaining alkaline process solution comprising glycine, is optionally concentrated and finally recirculated (process step d)).

Figure 1:
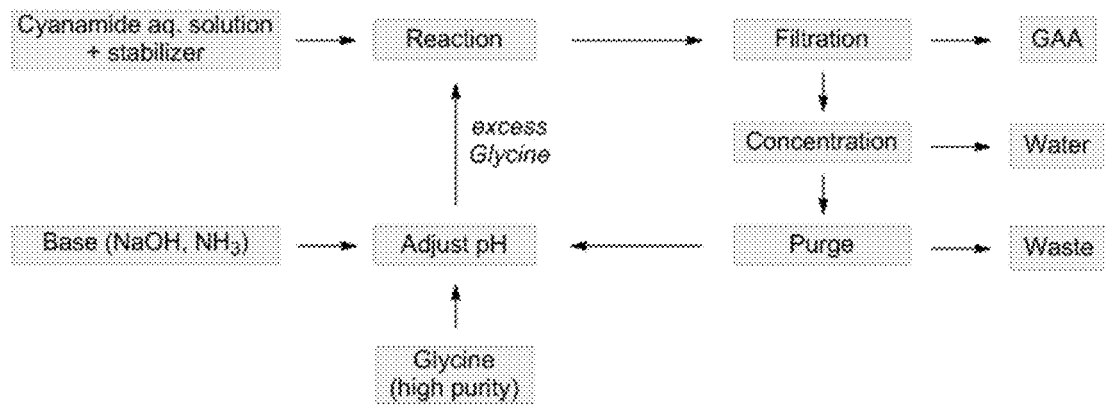
FIG. 1 shows a state-of-the art flow chart for the GAA process.
Figure 2:
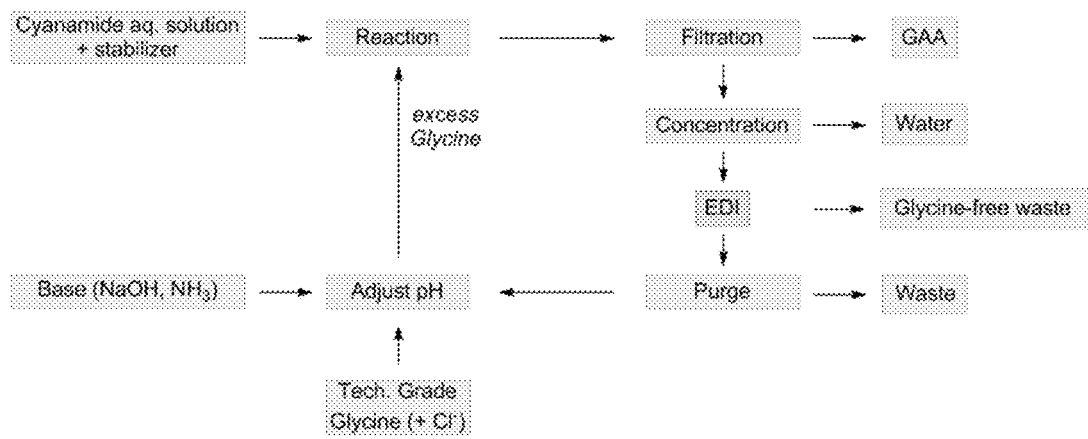
FIG. 2 depicts a process flow chart according to one embodiment of the present invention. The position of the electrodialysis cell within the GAA process can be freely chosen. For example, the EDI cell may also be located after pH adjustment, after reaction, after filtration or after purge.

The electrodialysis step may be conducted at any point in the GAA process. For example, the EDI step may be conducted after separating off the GAA product, as depicted in FIG. 2.

As an alternative, EDI may be conducted immediately after pH adjustment in step a).

EDI is operated with a current density in the electrodialysis cell in the range of 1 to 750 A/m$^2$, preferably in the range of 100 to 350 A/m$^2$.

The distance between the membranes should be at least 150 µm, in particular at least 250 µm and preferably 500 µm. This applies for all embodiments of the present invention, in particular for the stack embodiment as well as for the four-compartment embodiment.

The anionic impurities removed from the process solution by electrodialysis are mainly chloride and phosphate, as originating from technical grade glycine and/or cyanamide stabilization. However, also sulfur-containing anionic impurities, such as sulfates, sulfides, or sulfites, as occurring in cyanamide solutions, may be removed from the GAA process via electrodialysis.

The process according to the present invention may be carried out batchwise or (semi-) continuously. For the batch process, the expression "recirculating the alkaline process solution" is to be understood as re-using the alkaline process solution in a further batch.

Preferably, the process according to the present invention is carried out in a continuous or semi-continuous manner In the following, the invention is illustrated by non-limiting examples and exemplifying embodiments.

EXAMPLES

Material and Methods
Electrodialysis

The electrodialysis cell contains four compartments/chambers separated by three ion-selective exchange membranes (see FIG. 3). In the middle of the cell there is an anion exchange membrane (AEM). Towards the electrodes a cation exchange membrane (CEM) is used. The membrane areas are 201.5 cm². The membrane distance is 500 μm.

GAA Process Solution
11.4 wt. % glycine
0.7 wt. % GAA
0.3 wt. % dicyandiamide (DCA)
1.4 wt. % chloride
1.4 wt. % phosphate
Water ad 100 wt. %
pH=9.7

Examples

Example 1: Electrodialyis of GAA Process Solution

Two solutions for electrodialyis with a volume of 1 l were prepared first:
a 0.5 molar sulfuric acid solution, and
a NaCl solution with 2 g/l NaCl.

The sulfuric acid solution is pumped into the outer chambers (1) and (4), cf. FIG. 3. The NaCl solution flows through chamber (3) and the process solution described above is treated in chamber (2).

Initially, a current of 0.5 A was set, which was increased to 2 A during the experiment. The duration of the test is 15 hours.

After each hour, the electrical conductivity, the pH value and the composition of the solutions are determined.

The chloride content is reduced from an initial concentration of 1.36% by weight to a final concentration of 0.08% by weight. A chlorine reduction of the process solution of 1.28 wt. % was achieved. The energy requirement is 61 Wh and the power yield 43%.

Example 2: Electrodialyis of GAA Process Solution

The test setup is identical to that in Example 1. During the test only the current strength and duration of the test were changed.

A process solution as described above is treated with electrodialysis. The chloride content is reduced from an initial concentration of 1.37% by weight to a final concentration of 0.2% by weight.

The current was 2 A throughout the electrodialysis and the duration was 5 hours.

In this test, a chlorine reduction of the process solution of 1.17 wt. % was achieved. The required energy was 24 Wh and the current yield was 88%.

The chloride content is reduced from an initial concentration of 1.37% by weight to a final concentration of 0.2% by weight. At the same time, phosphate was reduced from an initial amount of 4190 ppm to 1770 ppm.

Example 3: pH-Dependence of GAA Yield

Reaction Conditions:
glycine concentration in the starting material solution: 25 wt. % (ratio glycine/cyanamide 2:1)
pH: 9.6
reaction temperature: 88-90° C.

The pH-adjusted glycine solution was placed in a three-neck round flask and preheated to 70C. This solution was then pumped simultaneously with the cyanamide solution into the reaction vessel heated with a thermostat to 88-90° C. The residence time was 13 minutes.

| | pH | GAA[a] [wt.-%] | Glycine[a] [wt.-%] | Cyanamide[a] [wt.-%] | yield GAA[b] [%] |
|---|---|---|---|---|---|
| 1 | 5.0 | 8.5 | | | 8 |
| 2 | 6.0 | —[c] | | | 8 |
| 3 | 7.0 | 37 | | | 11 |
| 4 | 8.0 | 58 | | | 23 |
| 5 | 8.5 | 99 | 3.7 | 0 | 39 |
| 6 | 9.0 | 99 | 2.3 | 0 | 38 |
| 7 | 9.6 | 99 | 3.1 | 0 | 76 |
| 8 | 10.0 | 95 | 8.6 | 0 | 38 |
| 9 | 12.0 | 82 | | | 13 |
| 10 | 12.5 | —[c] | | | 13 |
| 11 | 8.0 | 99 | 0 | 0 | 64 |
| 12 | 9.0 | 97 | 0 | 0 | 82 |
| 13 | 9.6 | 93 | 0 | 0 | 83 |
| 14 | 10.0 | 94 | 0 | 0 | 19 |
| 15 | 11.0 | 98 | 0 | 0 | 45 |

[a] The content of the solid was determined by HPLC analysis.
[b] The yield is related to cyanamide.
[c] No solids have precipitated. The yields were calculated from the corresponding analyses of the reaction solutions.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A process for preparing guanidino acetic acid (GAA), comprising:
    (a) preparing an alkaline process solution comprising glycine;
    (b) reacting cyanamide with the excess glycine in the alkaline process solution;
    (c) separating off the guanidino acetic acid product; and
    (d) recirculating the alkaline process solution comprising glycine;
    wherein anionic impurities are removed from the process solution by electrodialysis conducted in a cell comprising at least one feed compartment comprising the alkaline process solution and at least one concentrate compartment, and wherein the pH of the alkaline process solution is between 8.5 and 11.

2. The process of claim 1, wherein the at least one feed compartment is interconnected with the at least one concentrate compartment by an ion-selective anion exchange membrane (AEM).

3. The process of claim 2, wherein the at least one feed compartment and the at least one concentrate compartment are each independently connected with another compartment by an ion-selective cation exchange membrane (CEM).

4. The process of claim 1, wherein the electrodialysis cell comprises a stack of alternating feed compartments and concentrate compartments, the compartments being formed by alternating ion-selective anion exchange membranes and ion-selective cation exchange membranes.

5. The process of claim 1, wherein the electrodialysis cell is configured as a four compartment cell, the compartments being interconnected by three ion-selective exchange membranes.

6. The process of claim 1, wherein the electrodialysis cell comprises two outer compartments comprising a solution of sulfuric acid, each compartment being located between an electrode an outer ion-selective cation exchange membrane.

7. The process of claim 1, wherein the pH of the alkaline process solution is between 9 and 10.

8. The process according of claim 1, wherein the cyanamide is introduced into the process as an aqueous solution comprising at least one stabilizing agent.

9. The process of claim 8, wherein the at least one stabilizing agent is present in an amount of between 0.005 wt. % and 3 wt. %, based on the cyanamide solution.

10. The process of claim 8, wherein the at least one stabilizing agent is selected from the group consisting of: phosphoric acid, formic acid; esters of formic acid; magnesium chloride; magnesium sulfate; and mixtures thereof.

11. The process of claim 1, wherein, for process step (a), the ratio of cyanamide to glycine is in the range of between 1.1:1 and 10:1.

12. The process of claim 1, wherein, for process step (a), the ratio of cyanamide to glycine is in the range of between 1.5:1 and 2.5:1.

13. The process of claim 1, wherein the current density in the electrodialysis cell is in the range of 1 to 750 A/m$^2$.

14. The process of claim 1, wherein the anionic impurities removed from the process solution by electrodialysis are chloride, phosphate, sulfate, sulfide, or sulfite.

15. The process of claim 1, wherein the process is carried out in a continuous or semi-continuous manner.

16. The process of claim 2, wherein the at least one feed compartment and the at least one concentrate compartment are each independently connected with another compartment by an ion-selective cation exchange membrane and wherein the electrodialysis cell comprises a stack of alternating feed compartments and concentrate compartments, the compartments being formed by alternating ion-selective anion exchange membranes and ion-selective cation exchange membranes.

17. The process of claim 16, wherein the electrodialysis cell is configured as a four compartment cell, the compartments being interconnected by three ion-selective exchange membranes.

18. The process of claim 17, wherein the electrodialysis cell comprises two outer compartments comprising a solution of sulfuric acid, each compartment being located between an electrode and an outer ion-selective cation exchange membrane.

19. The process of claim 10, wherein, for process step (a), the ratio of cyanamide to glycine is in the range of between 1.1:1 and 10:1.

20. The process of claim 19, wherein the process is carried out in a continuous or semi-continuous manner.

* * * * *